United States Patent
Sumitani et al.

(10) Patent No.: US 11,225,679 B2
(45) Date of Patent: Jan. 18, 2022

(54) MUTANT β-GLUCOSIDASE

(71) Applicant: Kao Corporation, Tokyo (JP)

(72) Inventors: Junichi Sumitani, Sakai (JP); Yutaro Baba, Toyama (JP); Shuji Tani, Sakai (JP); Takashi Kawaguchi, Minoh (JP)

(73) Assignee: Kao Corporation, Tokyo (JP)

( * ) Notice: Subject to any disclaimer, the term of this patent is extended or adjusted under 35 U.S.C. 154(b) by 40 days.

(21) Appl. No.: 16/971,351

(22) PCT Filed: Feb. 21, 2019

(86) PCT No.: PCT/JP2019/006543
§ 371 (c)(1),
(2) Date: Aug. 20, 2020

(87) PCT Pub. No.: WO2019/167788
PCT Pub. Date: Sep. 6, 2019

(65) Prior Publication Data
US 2021/0024969 A1  Jan. 28, 2021

(30) Foreign Application Priority Data
Feb. 27, 2018 (JP) .............................. JP2018-033344

(51) Int. Cl.
*C12P 19/14* (2006.01)
*C12N 15/80* (2006.01)
(52) U.S. Cl.
CPC .............. *C12P 19/14* (2013.01); *C12N 15/80* (2013.01); *C12Y 302/01021* (2013.01)
(58) Field of Classification Search
CPC ....... C12N 9/2445; C12N 15/80; C12P 19/14; C12Y 302/01021

USPC ......................................................... 435/193
See application file for complete search history.

(56) References Cited

FOREIGN PATENT DOCUMENTS

| JP | 2012-029614 A | 2/2012 |
|---|---|---|
| JP | 2016-015894 A | 2/2016 |
| WO | WO 2013/115305 A1 | 8/2013 |

OTHER PUBLICATIONS

International Search Report for PCT/JP2019/006543; I.A. fd Feb. 21, 2019, dated May 21, 2019 from the Japan Patent Office, Tokyo, Japan.
International Preliminary Report on Patentability (IPRP), Chapter I of the Patent Cooperation Treaty, including the Written Opinion, for PCT/JP2019/006543; I.A. fd Feb. 21, 2019, dated Aug. 27, 2020, by the International Bureau of WIPO, Geneva, Switzerland.
Morikawa, Y, "Research Frontier of Biomass Degrading Enzymes—Focused on Cellulases and Hemicellulases," A. Kondo et al., editors, 2012, CMC Publishing Co,. Ltd., Japan, pp. 10-19.
Suzuki, K, et al., Crystal structures of glycoside hydrolase family 3 β-glucosidase 1 from *Aspergillus aculeatus*. Biochem J. Jun. 1, 2013;452(2);211-21. doi: 10.1042/BJ20130054. PMID: 23537284.

*Primary Examiner* — Tekchand Saidha
(74) *Attorney, Agent, or Firm* — Sterne, Kessler, Goldstein & Fox P.L.L.C.

(57) ABSTRACT

Provision of a mutant β-glucosidase having high protease resistance. A mutant β-glucosidase consists of an amino acid sequence having at least 90% sequence identity to SEQ ID NO: 1, wherein the amino acid sequence comprises Gln and Thr respectively at positions corresponding to positions 649 and 655 of SEQ ID NO: 1 or Tyr-Glu-Pro-Ala-Ser-Gly in a region corresponding to the region from position 653 to position 658 of SEQ ID NO: 1, and has β-glucosidase activity.

20 Claims, 2 Drawing Sheets
Specification includes a Sequence Listing.

[Figure 1]
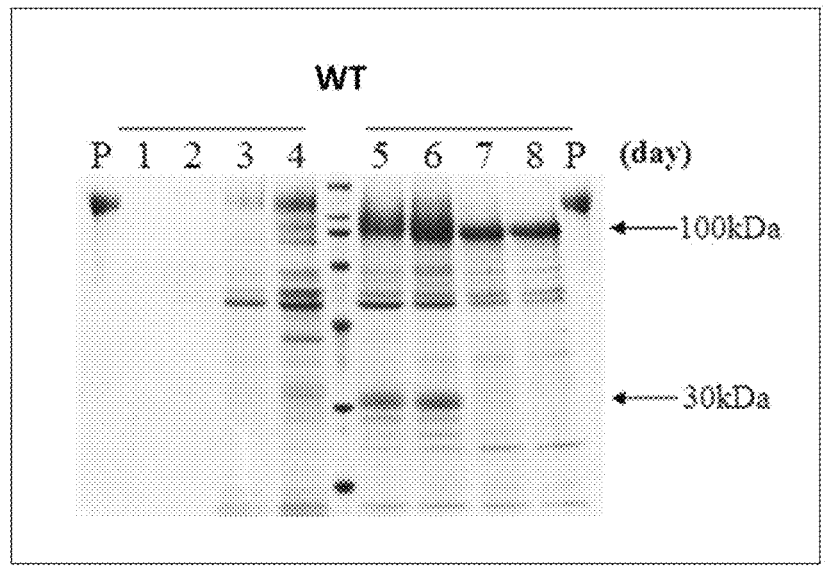
[Figure 2]
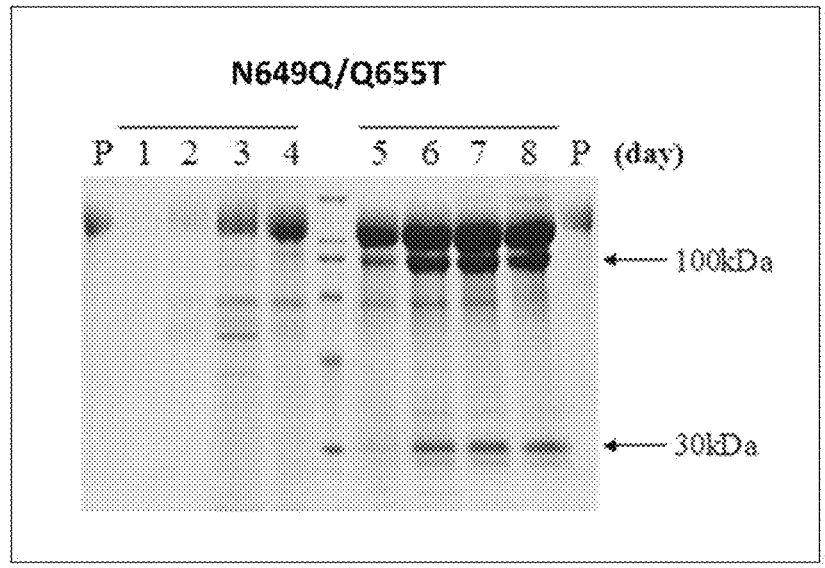

[Figure 3]
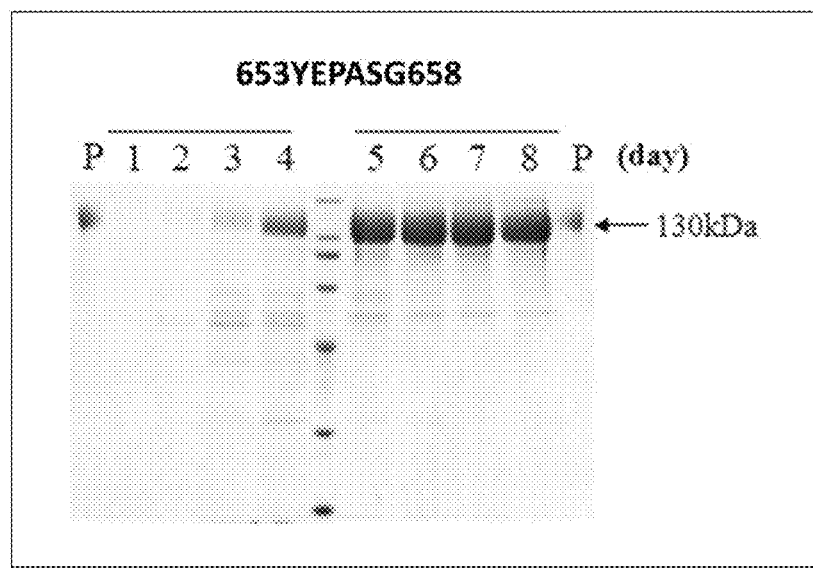

MUTANT β-GLUCOSIDASE

FIELD OF THE INVENTION

The present invention relates to a mutant β-glucosidase.

BACKGROUND OF THE INVENTION

A technology is known for producing a saccharide from cellulose in a biomass material containing cellulose (hereinafter, sometimes refers to as "biomass") and converting the saccharide to energies such as ethanol and chemical products using a fermentation method. Efforts made on environmental issues in recent years have helped advancement in various technological development for the industrial use of biomasses, and mass production of fuels and chemical products using biomasses has also been realized.

Biomass is made up of cellulose fibers, hemicelluloses surrounding the cellulose fibers and containing mainly xylan, and lignin. In the production of a saccharide using biomass as a raw material, it is important to increase saccharification efficiency of celluloses and hemicelluloses and the achievement thereof requires a biomass saccharification enzyme such as a cellulase and a hemicellulase which hydrolyzes cellulose and hemicellulose. For example, for efficiently degrading cellulose into glucose, at least three types of cellulases need to work in concert with each other, such as (1) a cellobiohydrolase (CBH) which cleaves off a saccharide in a cellobiose unit from the end of crystalline and non-crystalline cellulose fibers, (2) an endoglucanase (EG) which makes a cleavage into the cellulose chain by working on the non-crystalline cellulose, and (3) a β-glucosidase (BGL) which produces glucose by hydrolyzing the cellobiose produced by these enzymes.

Fungi well known for producing a cellulase used for the saccharification of biomass are microorganisms belonging to the genus *Trichoderma* such as *Trichoderma reesei* and *Trichoderma viride*. However, in the biomass saccharification using a cellulose derived from a microorganism belonging to the genus *Trichoderma*, relatively low β-glucosidase activity is noted (Non Patent Literature 1). A technology has been developed for increasing biomass saccharification activity of an enzyme derived from a microorganism belonging to the genus *Trichoderma* by expressing a β-glucosidase of *Aspergillus aculeatus* in the microorganism belonging to the genus *Trichoderma* (for example, Non Patent Literature 1, Patent Literature 1).
(Patent Literature 1) International WO 2013/115305 A1
(Non Patent Literature 1) MORIKAWA Yasushi, Research Frontier of Biomass Degrading Enzymes, 2012, CMC Publishing Co., Ltd., p 10-19

SUMMARY OF THE INVENTION

The present invention provides a mutant β-glucosidase selected from the group consisting of the following (i), (ii), and (iii):

(i) a polypeptide that consists of an amino acid sequence obtained by substituting, with Gln and Thr, an amino acid residue at a position corresponding to position 649 of SEQ ID NO: 1 and an amino acid residue at a position corresponding to the position 655 of SEQ ID NO: 1, respectively, in an amino acid sequence as set forth in SEQ ID NO: 1, or an amino acid sequence having at least 90% identity thereto, and has β-glucosidase activity;

(ii) a polypeptide that consists of an amino acid sequence obtained by substituting, with Tyr-Glu-Pro-Ala-Ser-Gly, an amino acid sequence of a region corresponding to the region from position 653 to position 658 of SEQ ID NO:1 in an amino acid sequence as set forth in SEQ ID NO: 1, or an amino acid sequence having at least 90% identity thereto; and (iii) a polypeptide that comprises the polypeptide of (i) or (ii) and has β-glucosidase activity.

Further, the present invention provides a polynucleotide encoding the mutant β-glucosidase.

Further, the present invention provides a vector comprising the polynucleotide.

Further, the present invention provides a transformant comprising the polynucleotide or the vector.

Further, the present invention provides a biomass saccharification agent comprising the mutant β-glucosidase.

Further, the present invention provides a method for producing a saccharide comprising saccharifying a biomass using the mutant β-glucosidase.

The present invention further provides a method for producing a mutant β-glucosidase, comprising (a) substituting, with Gln and Thr, an amino acid residue at a position corresponding to position 649 of SEQ ID NO: 1 and an amino acid residue at a position corresponding to position 655 of SEQ ID NO: 1, respectively, in a polypeptide that comprises the amino acid sequence as set forth in SEQ ID NO: 1, or an amino acid sequence having at least 90% identity thereto, and that has β-glucosidase activity or (b) substituting, with Tyr-Glu-Pro-Ala-Ser-Gly, an amino acid sequence of a region corresponding to the region from position 653 to position 658 of SEQ ID NO:1 in a polypeptide that comprises the amino acid sequence as set forth in SEQ ID NO: 1, or an amino acid sequence having at least 90% identity thereto, and has β-glucosidase activity.

BRIEF DESCRIPTION OF DRAWINGS

FIG. 1 SDS-PAGE analysis results on expression products of a wild-type AaBGL1 expression strain. The number above each lane shows the number of culture day, and P represents purified AaBGL1.

FIG. 2 SDS-PAGE analysis results on expression products of an N649Q/Q655T mutant expression strain. The number above each lane shows the number of culture days, and P represents a purified mutant.

FIG. 3 SDS-PAGE analysis results on expression products of a 653YEPASG658 mutant expression strain. The number above each lane shows the number of culture days, and P represents a purified mutant.

DETAILED DESCRIPTION OF THE INVENTION

In the present Description, the "amino acid residue" means 20 types of amino acid residue constituting a protein such as alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

In the present Description, the identity between amino acid sequences and between nucleotide sequences can be calculated by Lipman-Pearson method (Science, 1985, 227: 1435-41). Specifically, the calculation can be achieved by carrying out an analysis using a homology analysis (Search homology) program of a genetic information processing software Genetyx-Win (Ver.5.1.1; Software Development) with the Unit size to compare (ktup) being set to 2.

In the present Description, the "at least 90% identity" described pertaining to an amino acid sequence and a nucleotide sequence refers to 90% or more, more preferably 95% or more, further preferably 98% or more, further preferably 99% or more, further preferably 99.5% or more, further preferably 99.6% or more, further preferably 99.7% or more, and further preferably 99.8% or more identity.

In the present Description, the "one to several" pertaining to the deletion, substitution or addition of an amino acid(s) means preferably from 1 to 160 amino acids, more preferably from 1 to 80 amino acids, further preferably from 1 to 40 amino acids, further preferably from 1 to 20 amino acids, further preferably from 1 to 10 amino acids, and further preferably from 1 to 5 amino acids.

In the present Description, the "position corresponding to" and "region corresponding to" on an amino acid sequence and a nucleotide sequence can be determined by aligning a sequence of interest and a reference sequence (for example, the amino acid sequence as set forth in SEQ ID NO: 1) such that the maximum homology is given to conserved amino acid residues or nucleotides present in each amino acid sequence or nucleotide sequence. The alignment can be carried out using a publicly known algorithm and the procedure therefor is publicly known by those skilled in the art. For example, the alignment can be carried out using a Clustal W multiple alignment program (Nucleic Acids Res, 1994, 22:4673-4680) in default settings. Alternatively, Clustal W2 and Clustal omega, revised versions of Clustal W, can also be used. Clustal S, Clustal W2, and Clustal omega can be used on the websites of, for example, European Bioinformatics Institute (EBI [www.ebi.ac.uk/index.html]) and DNA Data Bank of Japan (DDBJ [www.ddbj.nig.ac.jp/Welcome-j.html]) operated by National Institute of Genetics.

Those skilled in the art can make further fine adjustments on the alignment obtained in the above as needed to achieve the optimum alignment. Such optimum alignment is preferably determined considering the similarity of amino acid sequence and frequency of inserted gaps. The similarity of amino acid sequences herein refers to, when two amino acid sequences are aligned, the percentage (%) of the number of positions at which identical or analogous amino acid residues are present in the two sequences, relative to the number of full-length amino acid residues. Analogous amino acid residues mean, of 20 types of amino acids constituting a protein, amino acid residues having similar properties with each other in the aspect of polarity and electric charge, so called, amino acid residues which cause conservative substitution. The groups consisting of such analogous amino acid residues are well known by those skilled in the art and examples include, but not limited thereto, arginine and lysine; glutamic acid and aspartic acid; serine and threonine; glutamine and asparagine; valine, leucine, and isoleucine, respectively.

The position of amino acid residue or nucleotide on the sequence of interest aligned to position corresponding to any position of the reference sequence by the alignment mentioned above is considered as the "position corresponding to" such any position, and the amino acid residue or nucleotide at the position is referred to as the "amino acid residue at a position corresponding to" or "nucleotide at a position corresponding to". Further, the region of a sequence of interest aligned to region corresponding to any region of the reference sequence by the alignment mentioned above is considered as the "region corresponding to" such any region, and the amino acid sequence or nucleotide sequence of the region is referred to as the "amino acid sequence of a region corresponding to" or "nucleotide sequence of a region corresponding to".

In the present Description, the "β-glucosidase" (or also referred to as "BGL") refers to a polypeptide having β-glucosidase activity. In the present Description, the "β-glucosidase activity" refers to activity hydrolyze β-glucosidic bonds of a saccharide, and preferably refers to activity to hydrolyze cellobiose and produce glucose. The β-glucosidase activity of a protein can be determined through the pNP (p-Nitrophenol) method by, for example, measuring an amount of pNP released by enzymatic degradation from 4-nitrophenyl-β-D-glucopyranoside. Specific procedures for measuring the β-glucosidase activity are described in detail in examples to be described later.

In the present Description, the "biomass" refers to cellulosic biomass containing cellulose produced by plants and algae. Specific examples of the biomass include at least one selected from the group consisting of various wood materials obtained from conifers such as Japanese larch and bald cypress and broad-leaf trees such as oil palm (trunk) and Japanese cypress; processed or ground wood materials such as wood chips; pulps such as wood pulp produced from wood materials and cotton linter pulp obtained from fibers around cottonseed; papers such as newspaper, cardboard, magazine, and wood free paper; stem, leaf, and fruit of plants such as bagasse (residue that remains after sugarcane are crushed), palm Empty Fruit Bunch (EFB), rice straw, and cornstalk or leave; plant shells such as chaff, palm shell, and coconut shell; and algae. Of these, wood materials, processed or ground wood materials, and stem, leaf, and fruit of plants are preferable, bagasse, EFB, and oil palm (trunk) are more preferable, and bagasse is further preferable, from a viewpoint of easy availability and raw material cost. These kinds of biomass may be used singly or two or more may be used in mixture. Further, the above biomass may be dried.

The present invention provides a β-glucosidase mutant capable of more efficiently saccharifying biomass.

The present inventors found that the β-glucosidase produced by a microorganism and derived from the genus *Aspergillus* is cleaved into two polypeptides of about 100 kDa and about 30 kDa by a protease derived from such a microorganism. These cleaved 2 polypeptides are bound by a noncovalent bond and work as a single protein maintaining the same three-dimensional structure as before the cleavage, and thus the cleavage itself does not affect the β-glucosidase activity of an enzyme. However, the enzyme is further broken down triggered by this cleavage and the β-glucosidase activity will be lost.

The present inventors analyzed the N-terminal amino acid sequence of the about 30 kDa polypeptide of the cleaved β-glucosidase of the genus *Aspergillus* and identified that the cleavage site of the protease is the N-terminal V675. This region is identified as a disorder region in which the position of the main chain cannot be specified by an X-ray crystallography (Biochem J, 2013, 452(2):211-221), and it is thus presumed that the region is susceptible to attacks by a protease or the like due to the lack of specific structure. Thus, the present inventors introduced a mutation close to the cleavage site in the β-glucosidase and investigated an impact on the protease cleavage. As a result, a mutant with high protease resistance was found.

The mutant β-glucosidase of the present invention has high protease resistance, is not degraded by a protease in a medium when produced by a microorganism, and can retain a high yield and β-glucosidase activity.

The present invention provides a mutant β-glucosidase. The mutant β-glucosidase of the present invention can be produced by modifying a β-glucosidase having the amino acid sequence as set forth in SEQ ID NO: 1, or an amino acid sequence having at least 90% identity thereto, to substitute an amino acid residue at a predetermined position or an amino acid sequence of a predetermined region. The mutant β-glucosidase of the present invention has high protease resistance compared to the β-glucosidase before the substitution (parent β-glucosidase) and is less likely to be degraded by a protease. Thus, the mutant β-glucosidase of the present invention, when produced by a microorganism, is not degraded by a protease derived from the microorganism present in a medium and can hence retain a high yield and activity.

Thus, in an embodiment, the present invention provides a mutant β-glucosidase consisting of an amino acid sequence having at least 90 identity to the amino acid sequence as set forth in SEQ ID NO: 1, wherein the amino acid sequence contains Gln and Thr respectively at positions corresponding to position 649 and position 655 of SEQ ID NO: 1, or Tyr-Glu-Pro-Ala-Ser-Gly in a region corresponding to the region form position 653 to position 658 of SEQ ID NO: 1, and has β-glucosidase activity.

In a preferable embodiment, the mutant β-glucosidase of the present invention is selected from the group consisting of the following (i), (ii), and (iii):

(i) a polypeptide that consists of an amino acid sequence obtained by substituting, with Gln and Thr, an amino acid residue at a position corresponding to position 649 of SEQ ID NO:1 and an amino acid residue at a position corresponding to position 655 of SEQ ID NO:1, respectively, in the amino acid sequence as set forth in SEQ ID NO: 1, or an amino acid sequence having at least 90% identity thereto, and has β-glucosidase activity;

(ii) a polypeptide that consists of an amino acid sequence obtained by substituting, with Tyr-Glu-Pro-Ala-Ser-Gly, an amino acid sequence of a region corresponding to the region from position 653 to position 658 of SEQ ID NO:1 in the amino acid sequence as set forth in SEQ ID NO: 1, or an amino acid sequence having at least 90% identity thereto, and has β-glucosidase activity;

(iii) a polypeptide that comprises the polypeptide of (i) or (ii) and has β-glucosidase activity.

In another embodiment, the present invention provides a method for producing a mutant β-glucosidase. The method comprises the following (a) or (b):

(a) substituting, with Gln and Thr, an amino acid residue at a position corresponding to position 649 of SEQ ID NO:1 and an amino acid residue at a position corresponding to position of 655 of SEQ ID NO:1, respectively, in a polypeptide that comprises the amino acid sequence as set forth in SEQ ID NO: 1, or an amino acid sequence having at least 90% identity thereto, and has β-glucosidase activity; or (b) substituting, with Tyr-Glu-Pro-Ala-Ser-Gly, an amino acid sequence of a region corresponding to the region from position 653 to position 658 of SEQ ID NO:1 in a polypeptide that comprises the amino acid sequence as set forth in SEQ ID NO: 1, or an amino acid sequence having at least 90% identity thereto, and has β-glucosidase activity.

In the mutant β-glucosidase of the present invention or the production method thereof, preferable examples of the amino acid sequence as set forth in SEQ ID NO: 1, or an amino acid sequence having at least 90% identity thereto, include an amino acid sequence as set forth in SEQ ID NO: 1 or 2; and an amino acid sequence having deletion, substitution or addition of one to several amino acids with respect to the amino acid sequence as set forth in SEQ ID NO: 1 or 2 (provided that the amino acid sequences has at least 90% identity to SEQ ID NO: 1).

In the present Description, a β-glucosidase, before the above amino acid substitution, containing the amino acid sequence as set forth in SEQ ID NO: 1, or an amino acid sequence having at least 90% identity thereto, is sometimes referred to as the parent β-glucosidase of the mutant glucosidase of the present invention (or simply the parent β-glucosidase or parent BGL). In the parent BGL, i) amino acid residues at a position corresponding to position 649 of SEQ ID NO:1 is not Gln and the amino acid residue at a position corresponding to position 655 of SEQ ID NO:1 is not Thr; ii) an amino acid sequence in a region corresponding to the region from position 653 to position 658 of SEQ ID NO: 1 is not Tyr-Glu-Pro-Ala-Ser-Gly; or iii) both i) and ii).

Examples of the parent BGL, include β-glucosidase of *Aspergillus aculeatus* consisting of the amino acid sequence as set forth in SEQ ID NO: 1 (in the present Description, also referred to as AaBGL1, GenBank: BAA10968.1, UniProtKB/Swiss-Prot: P48825.1).

Other examples of the parent BGL include a polypeptide consisting of an amino acid sequence having at least 90% identity to the amino acid sequence as set forth in SEQ ID NO: 1 and having β-glucosidase activity. Examples of such a polypeptide include a BGL derived from the genus *Aspergillus* and consisting of an amino acid sequence having at least 90% identity to the amino acid sequence as set forth in SEQ ID NO: 1.

Other examples of the parent BGL include a mutant of AaBGL1 (SEQ ID NO: 1) mentioned above. Examples of such a mutant include a β-glucosidase consisting of an amino acid sequence having deletion, substitution or addition of one to several amino acids with respect to the amino acid sequence as set forth in SEQ ID NO: 1. Such a mutant may be a naturally occurred mutant or may be artificially prepared.

Other examples of the parent BGL include a BGL preprotein in which AaBGL1 (SEQ ID NO: 1) mentioned above or a mutant thereof and a secretion signal sequence are bound. Preferable examples of the preprotein include a preprotein of AaBGL1 with a secretion signal sequence, consisting of the amino acid sequences as set forth in SEQ ID NO: 2. Other examples of the preprotein include a BGL preprotein consisting of an amino acid sequence having deletion, substitution or addition of one to several amino acids with respect to the amino acid sequence as set forth in SEQ ID NO: 2 (provided that the amino acid sequence has at least 90% identity to SEQ ID NO: 1).

Preferably, the parent BGL mentioned above has Asn at a position corresponding to position 649 and Gln at a position corresponding to position 655 of the amino acid sequence as set forth in SEQ ID NO: 1. Further preferably, the parent BGL has Asn-Ala-Gln-Val-Ala-Thr in a region corresponding to the region from position 653 to position 658 of SEQ ID NO: 1. More preferably, the parent BGL has Asn at a position corresponding to position 649 and Gln at a position corresponding to position 655 of the amino acid sequence as set forth in SEQ ID NO: 1, and Asn-Ala-Gln-Val-Ala-Thr in a region corresponding to the region from position 653 to position 658 of SEQ ID NO: 1.

The mutant BGL of the present invention can be produced by, for example, expressing a polynucleotide encoding the mutant BGL of the present invention. Preferably, the mutant BGL of the present invention can be produced from a transformant into which a polynucleotide encoding the mutant BGL is introduced. Namely, the mutant BGL of the present invention is produced when a polynucleotide encoding the mutant BGL of the present invention or a vector containing such a polynucleotide is introduced into a host cell to obtain a transformant, and subsequently the transformant is cultured in a suitable medium to express the introduced polynucleotide. The mutant BGL of the present invention can be obtained by isolating or purifying the produced mutant BGL from the culture product.

Thus, the present invention further provides a polynucleotide encoding the mutant BGL of the present invention, and a vector containing such a polynucleotide. The present invention further provides a method for producing a transformant including introducing a polynucleotide encoding the mutant BGL of the present invention or a vector containing such a polynucleotide into a host cell. The present invention further provides a transformant containing such a polynucleotide or vector. The present invention further provides a method for producing a mutant BGL including culturing such a transformant.

The polynucleotide encoding the mutant BGL of the present invention may encompass single strand or double strand DNA, cDNA, RNA, and other artificial nucleic acids. These DNA, cDNA, and RNA may be chemically synthesized. Further, the polynucleotide of the present invention may also contain a nucleotide sequence of an untranslated region (UTR) in addition to open reading frames (ORF).

The polynucleotide encoding the mutant BGL of the present invention can be genetically engineered or chemically synthesized based on the amino acid sequence of the mutant BGL. For example, the polynucleotide encoding the mutant glucosidase of the present invention can be prepared by, in the polynucleotide encoding the parent BGL mentioned above (hereinafter also referred to as the parent BGL gene), mutating a nucleotide sequence (codon) encoding amino acid residues at positions corresponding to positions 649 and 655 of SEQ ID NO: 1 to a nucleotide sequence (codon) encoding Gln and Thr, respectively. Alternatively, the polynucleotide encoding the mutant glucosidase of the present invention can be prepared by, in a parent BGL gene, mutating a nucleotide sequence (codon) encoding a region corresponding to the region from position 653 to position 658 of SEQ ID NO: 1 to a nucleotide sequence (codon) encoding Tyr-Glu-Pro-Ala-Ser-Gly. Expression of such a mutated polynucleotide enables the obtention of the mutant BGL in which the amino acid residues or sequence to be substituted is substituted with the amino acid residues or the sequence of interest.

Examples of the parent BGL gene include the polynucleotide encoding AaBGL1 as set forth in SEQ ID NO: 1 and the polynucleotide encoding the preprotein (SEQ ID NO: 2) having a secretion signal sequence thereof as mentioned above. Preferable examples include a polynucleotide consisting of the nucleotide sequence as set forth in SEQ ID NO: 3. Such a polynucleotide can be obtained by any method used in the related fields. For example, the polynucleotide encoding the amino acid sequence as set forth in SEQ ID NO: 1 can be obtained by extracting the whole genome DNA of *A. aculeatus*, subsequently selectively amplifying a target nucleic acid by PCR using primers designed based on the sequence of SEQ ID NO: 3, and purifying the amplified nucleic acid.

Alternatively, examples of the parent BGL gene include a polynucleotide encoding the parent BGL mentioned above which consists of an amino acid sequence having at least 90% identity to the amino acid sequence as set forth in SEQ ID NO: 1. Examples of such a polynucleotide include a polynucleotide encoding a mutant of AaBGL1 mentioned above. The parent BGL gene may be a naturally occurred gene or may be artificially prepared based on the sequence of SEQ ID NO: 1. For example, a mutation is introduced into a gene encoding the amino acid sequence of SEQ ID NO: 1 (for example, SEQ ID NO: 3) by a publicly known mutagenesis method such as ultraviolet irradiation and site directed mutagenesis, and the β-glucosidase activity of the polypeptide encoded by the obtained mutant gene is investigated. Selection of the gene encoding the polypeptide having the desired activity enables the obtention of the parent BGL gene. The gene sequence can be confirmed by sequencing as needed. The procedures of such a mutation are well known by those skilled in the art.

Introduction of a mutation of interest into the parent BGL gene can be carried out using various site directed mutagenesis methods well known by those skilled in the art. The site directed mutagenesis method can be carried out by any technique such as, for example, inverse PCR method and annealing method (by Muramatsu et al. version, "Kaitei Dai4 pan Shin Idenshi Kogaku Handobukku (in Japanese)" ("Revised 4th Edition, New Gene Engineering Handbook"), Yodosha Co., Ltd., p. 82-88). Various commercially available kits for site directed mutagenesis such as QuickChange II Site-Directed Mutagenesis Kit and QuickChange Multi Site-Directed Mutagenesis Kit by Stratagene Inc can also be used as needed. Alternatively, the site directed mutagenesis into the parent BGL gene can be carried out by publicly known techniques such as SOE (splicing by overlap extension)—PCR method (Horton R. M. et al, Gene, 1989, 77(1):61-68) and megaprimer method.

For example, the site directed mutagenesis into the parent BGL gene can be carried out using mutation primers containing a nucleotide mutation to be introduced. Such mutation primers may be designed such that they anneal to a region containing a nucleotide sequence encoding the t amino acid residue to be substituted in the parent BGL gene and contain a nucleotide sequence having a nucleotide sequence (codon) encoding amino acid residues after substitution in place of a nucleotide sequence (codon) encoding the amino acid residue to be substituted. Those skilled in the art can suitably recognize and select the nucleotide sequence (codon) encoding the amino acid residue to be substituted and the amino acid residue substituted based on a typical textbook.

Mutation primers can be prepared by well-known oligonucleotide synthesis method such as phosphoramidite method (Nucleic Acids Research, 17, 7059-7071, 1989). Further, mutation primers can also be prepared using, for example, a commercially available oligonucleotide synthesizer (manufactured by ABI). When the site directed mutagenesis as described above is carried out using a primer set containing mutation primers and the parent BGL gene as a template DNA, the polynucleotide encoding a mutant BGL of interest can be obtained.

The vector containing the polynucleotide encoding the mutant BGL of the present invention can be prepared by introducing such a gene into a vector. Type of vector into which such a polynucleotide is introduced is not particularly limited and examples thereof includes a vector typically used for the protein production such as a plasmid, cosmid, phage, viruse, YAC, and BAC. Of these, a plasmid vector is preferable, and a plasmid vector inducing high expression of a protein is more preferable. Those skilled in the art can select a preferable vector depending on the type of host cell.

A Plasmid vector for protein expression may be prepared according to a host cell but a commercially available product may also be used. Examples of the vector include yeast expression vectors pNAN8142 (Biosci Biotechnol Biochem, 1996, 60:383-389) and pMA91 (Biosci Biotechnol Biochem, 1998, 62:1615-1618).

The vector can encompass a DNA fragment containing a DNA replication initiation region or a DNA region containing a replication point. Alternatively, in such a vector, a regulatory region such as a promoter region, a terminator region or a secretion signal region for extracellularly secreting the expressed protein may be operably linked to the above polynucleotide encoding the mutant BGL of the present invention. Alternatively, a marker gene (for example, drug resistance genes such as ampicillin, neomycin, kanamycin, and chloramphenicol) for selecting a host cell into which the vector is suitably introduced may further be incorporated. Alternatively, when an auxotrophic strain is used as a host cell into which the vector of the present invention is introduced, a vector containing a gene encoding a nutrient required may be used.

Preferable examples of the regulatory region include P-No8142 promoter (Biosci Biotechnol Biochem, 1996, 60:383-389) and *Trichoderma reesei*-derived cbh1 promoter sequence (Curr Genet, 1995, 28(1):71-79). Alternatively, a promoter expressing a saccharification enzyme such as a cellobiohydrolase, endoglucanase, β-glucosidase, xylanase, and β xylosidase may be used. Alternatively, a promoter of a metabolic pathway enzyme such as a pyruvate decarboxylase, alcohol dehydrogenase, and pyruvate kinase may be used.

Linkage of the sequence encoding the mutant BGL of the present invention to the above regulatory region or marker gene sequence can be carried out by a method such as SOE-PCR method mentioned above. The procedure of introducing a gene sequence into the vector is well known in the related fields. The type of regulatory regions such as promoter region, terminator and secretion signal region is not particularly limited, and a promoter and a secretion signal sequence typically used can be suitably selected and used depending on a host cell into which they are introduced.

The transformant containing the polynucleotide encoding the mutant BGL of the present invention or the vector containing such a polynucleotide can be obtained by introducing the vector into a host cell or introducing the polynucleotide into the genome of a host cell. The method for introducing the vector into a host cell usable can be a method typically used in the related fields such as the protoplast method or the electroporation method. When a strain into which the introduction is suitably carried out is selected with the marker gene expression and auxotroph as an indicator, the transformant of interest into which the vector is introduced can be obtained.

The method for introducing the polynucleotide encoding the mutant BGL of the present invention into the genome of a host cell is not particularly limited but includes, for example, a double cross system using a DNA fragment containing such a polynucleotide. The DNA fragment may be introduced downstream of the promoter sequence of a gene with a high expression level in the host cell mentioned above, or a fragment in which the DNA fragment is operably linked to the regulatory region mentioned above is prepared in advance and the linked fragment may be introduced into the genome of a host cell. Further, the DNA fragment may be linked in advance to the marker (drug resistant gene and auxotrophic complementary gene) for selecting a cell into which the polynucleotide of the present invention is suitably introduced.

In the present Description, the polynucleotide encoding the BGL and the regulatory region are "operably linked" refers to that the polynucleotide and the regulatory region are arranged such that the BGL encoded by the polynucleotide can be expressed under the regulation of the regulatory region.

Examples of the host cell for such a transformant include a microorganism such as yeasts, bacterium, and filamentous fungus. Examples of the yeast include *Rhizopus oryzae*, *Saccharomyces cerevisiae*, and *Pichia pastoris*. Examples of the bacterium include *Escherichia coli*, and bacterium belonging to the genus *Staphylococcus*, the genus *Enterococcus*, the genus *Listeria*, and the genus *Bacillus*, and of which, *Escherichia coli* and the bacterium belonging to the genus *Bacillus* (for example, *Bacillus subtilis* or mutant strains thereof) are preferable. Examples of the *Bacillus subtilis* mutant strain include the nine-protease-deficient strain, KA8AX, described in J Biosci Bioeng, 2007, 104 (2):135-143 and the eight-protease-deficient having increased protein folding efficiency strain, D8PA, described in Biotechnol Lett, 2011, 33(9):1847-1852. Examples of the filamentous fungus include the genus *Trichoderma*, the genus *Aspergillus*, and the genus *Rhizopus*, and of which, the genus *Trichoderma* is preferable from a viewpoint of enzyme productivity.

When the thus obtained transformant into which the polynucleotide encoding the mutant BGL of the present invention or the vector containing such a polynucleotide is introduced is cultured in a suitable medium, the polynucleotide is expressed and the mutant BGL of the present invention is produced. The medium used for culturing such a transformant can be suitably selected by those skilled in the art depending on the type of transformant microorganism.

Alternatively, the mutant BGL of the present invention may be expressed from a polynucleotide encoding the mutant BGL of the present invention or a transcript thereof using a cell-free translation system. The "cell-free translation system" is an in vitro transcription translation system or an in vitro translation system constructed by adding a reagent such as an amino acid required for protein translation to a suspension obtained by mechanically disrupting cells to be the host cell.

The mutant BGL of the present invention produced in the above culture product or the cell-free translation system can be isolated or purified by using a routine method used for protein purification such as centrifugation, ammonium sulfate precipitation, gel chromatography, ion exchange chromatography, and affinity chromatography singly or in a suitable combination. At this time, when the polynucleotide encoding the mutant BGL and the secretion signal sequence are operably linked on the vector in the transformant, the obtained BGL is extracellularly secreted and thus can be easily collected from the culture product. The BGL collected from the culture product may further be purified by a publicly known means.

As shown in examples to be described later, the mutant β-glucosidase of the present invention has high protease resistance compared to the β-glucosidase before the mutation (parent BGL). As a result, the mutant β-glucosidase of the present invention, compared to the parent BGL, is less likely to be hydrolyzed by a protease in a medium when produced by a microorganism and hence retain high β-glucosidase activity and high yield (FIGS. 1 to 3).

The mutant β-glucosidase of the present invention is useful as an enzyme for biomass saccharification. Thus, the present invention further provides a biomass saccharification agent containing the mutant β-glucosidase of the present invention. The present invention further provides a method for producing a saccharide including saccharifying biomass using the mutant β-glucosidase of the present invention.

The biomass saccharification agent of the present invention is preferably an enzyme composition for biomass saccharification containing the mutant β-glucosidase of the present invention (hereinafter also referred to as the enzyme composition of the present invention). The enzyme composition of the present invention contains the mutant BGL of the present invention and preferably further contains additional biomass saccharification enzyme other than the mutant BGL of the present invention from a viewpoint of increasing the saccharification efficiency. The additional biomass saccharification enzyme may be an enzyme derived from an animal, plant, and microorganism. Examples of the additional biomass saccharification enzyme include an additional cellulase other than the mutant BGL of the present invention such as an endoglucanase, exoglucanase, cellobiohydrolase, and BGL other than the mutant BGL of the present invention, and a hemicellulase such as a xylanase, xylosidase, and galactanase, preferably an additional cellulase other than the mutant BGL of the present invention, and more preferably at least one selected from the group consisting of a cellobiohydrolase and endoglucanase. These biomass saccharification enzymes may be used singly or two or more of them may be used in combination. The enzyme composition of the present invention preferably contains, from a viewpoint of increasing the biomass saccharification efficiency, at least one selected from the group consisting of a cellobiohydrolase and endoglucanase.

Specific examples of the additional cellulase other than the mutant BGL of the present invention, which is contained in the enzyme composition of the present invention include, but not limited thereto, a cellulase derived from *Trichoderma reesei*; cellulase derived from *Trichoderma viride*; cellulases derived from various *Bacillus* strains such as *Bacillus* sp. KSM-N145 (FERM P-19727), *Bacillus* sp. KSM-N252 (FERM P-17474), *Bacillus* sp. KSM-N115 (FERM P-1972), *Bacillus* sp. KSM-N440 (FERM P-19728), and *Bacillus* sp. KSM-N659 (FERM P-19730); heat resistant cellulase derived from *Pyrococcus horikoshii*; and cellulase derived from *Humicola insolens*. Of these, a cellulase derived from *Trichoderma reesei*, *Trichoderma viride*, or *Humicola insolens* is preferable from a viewpoint of increasing the saccharification efficiency. Further, a recombinant cellulase obtained by expressing a cellulase gene exogenously introduced into the above microorganism may also be used. Specific examples include cellulase JN11 produced by X3AB1 strain (J Ind Microbiol Biotechnol, 2012, 1741-1749) obtained by introducing a β-glucosidase gene derived from *Aspergillus aculeatus* into *Trichoderma reesei*. Alternatively, a cellulase formulation containing the above additional cellulase may be contained in the enzyme composition of the present invention and used in combination with the mutant BGL of the present invention. Specific examples of the cellulase formulation include Cellcrust (registered trademark) 1.5 L (manufactured by Novozymes A/S), TP-60 (manufactured by Meiji Co., Ltd.), Cellic (registered trademark) CTec2 (manufactured by Novozymes A/S), Accellerase™DUET (manufactured by Genencor), and Ultraflo (registered trademark) L (manufactured by Novozymes A/S).

Specific examples of the cellobiohydrolase contained in the enzyme composition of the present invention include a cellobiohydrolase derived from *Trichoderma reesei*, *Trichoderma viride*, or *Humicola insolens*, and heat resistant cellobiohydrolase derived from *Pyrococcus horikoshii*. Of these, a cellobiohydrolase derived from *Trichoderma reesei*, *Trichoderma viride*, or *Humicola insolens* is preferable from a viewpoint of increasing the saccharification efficiency, and a cellobiohydrolase_derived from *Trichoderma reesei* is more preferable.

Specific examples of the endoglucanase contained in the enzyme composition of the present invention include an enzyme derived from *Trichoderma reesei*, *Acremonium celluloriticus*, *Humicola insolens*, *Clostridium thermocellum*, *Bacillus*, *Thermohifida*, and *Cellulomonas*. Of these, an enduglocanase derived from *Trichoderma reesei*, *Humicola insolens*, *Bacillus*, or *Cellulomonas* is preferable, and an endoglucanase derived from *Trichoderma reesei* are more preferable from a viewpoint of increasing the saccharification efficiency.

Examples of the additional BGL other than the mutant BGL of the present invention contained in the enzyme composition of the present invention include a BGL derived from *Aspergillus niger* (for example, Novozyme 188 manufactured by Novozymes A/S and BGL manufactured by Megazyme Ltd.) and a BGL derived from *Trichoderma reesei* or *Penicillium emersonii*. Of these, Novozyme 188 and a BGL derived from *Trichoderma reesei* are preferable, and a BGL derived from *Trichoderma reesei* is more preferable from a viewpoint of increasing the biomass saccharification efficiency.

Examples of the hemicellulase contained in the enzyme composition of the present invention include a hemicellulase derived from *Trichoderma reesei*; a xylanase derived from *Bacillus* sp. KSM-N546 (FERM P-19729); a xylanase derived from *Aspergillus niger*, *Trichoderma viride*, *Humicola insolens*, or *Bacillus alcalophilus*; a xylanase derived from *Thermomyces*, *Aureobasidium*, *Streptomyces*, *Clostridium*, *Thermotoga*, *Thermoascus*, *Caldocellum*, or *Thermomonospora*; a β-xylosidase derived from *Bacillus pumilus*; and a β-xylosidase derived from *Selenomonas ruminantium*. Of these, a xylanase derived from *Bacillus* sp., *Aspergillus niger*, *Trichoderma* or *Streptomyces* or a β-xylosidase derived from *Selenomonas ruminantium* is preferable, and a xylanase derived from *Bacillus* sp. or *Trichoderma viride* or a β-xylosidase derived from *Selenomonas ruminantium* is more preferable from a viewpoint of increasing the saccharification efficiency. Alternatively, examples of preferable hemicellulase include a mutant xylanase described in JP-A-2013-243953, JP-A-2013-243954, JP-A-2015-167552, JP-A-2016-119877, JP-A-2017-012006, and JP-A-2017-035001.

The content of the mutant BGL of the present invention in the biomass saccharification agent of the present invention (or the enzyme composition of the present invention) is, in the total protein amount, preferably 0.5 mass % or more, more preferably 1 mass % or more, and further preferably 2 mass % or more, and preferably 70 mass % or less, more preferably 50 mass % or less, further preferably 40 mass % or less, and further preferably 30 mass % or less, or, in the total protein amount, preferably from 0.5 to 70 mass %, more preferably from 1 to 50 mass %, further preferably from 2 to 40 mass %, and further preferably from 2 to 30 mass %. Preferably, the total protein amount of the biomass saccharification agent of the present invention (or the enzyme composition of the present invention) is from 3 to 25 mass %.

The content of the additional cellulase other than the mutant BGL of the present invention in the enzyme composition of the present invention is, in the total protein amount thereof, preferably 10 mass % or more, more preferably 30 mass % or more, and further preferably 50 mass % or more, and preferably 99 mass % or less, and more preferably 95 mass % or less, or, in the total protein amount thereof, preferably from 10 to 99 mass %, more preferably from 30 to 95 mass %, and further preferably from 50 to 95 mass %.

The content of endoglucanase in the enzyme composition of the present invention is, in the total protein amount thereof, preferably 1 mass % or more, more preferably 5 mass % or more, and further preferably 10 mass % or more, and preferably 70 mass % or less, more preferably 50 mass % or less, and further preferably 40 mass % or less, or, in the total protein amount thereof, preferably from 1 to 70 mass %, more preferably from 5 to 50 mass %, and further preferably from 10 to 40 mass %.

The content of the hemicellulase in the enzyme composition of the present invention is, in the total protein amount thereof, preferably 0.01 mass % or more, more preferably 0.1 mass % or more, and further preferably 0.5 mass % or more, and preferably 30 mass % or less, and more preferably 20 mass % or less, or, in the total protein amount thereof, preferably from 0.01 to 30 mass %, more preferably from 0.1 to 20 mass %, and further preferably from 0.5 to 20 mass %.

The method for producing a saccharide of the present invention includes saccharifying biomass using the above mutant BGL of the present invention. In the method, the enzyme composition of the present invention mentioned above may be used as the mutant BGL of the present invention. Conditions for the saccharification treatment in the method of the present invention are not particularly limited as long as the conditions do not deactivate the mutant BGL of the present invention and other enzyme(s) used in combination therewith. Suitable conditions can be suitably determined by those skilled in the art based on the type of biomass, procedures of pretreatment step(s), and the type of enzyme(s) to be used.

In the saccharification treatment, it is preferable to add the mutant BGL of the present invention to a suspension containing biomass. The content of biomass in the suspension is, from a viewpoint of increasing the saccharification efficiency or the saccharide production efficiency (namely, saving time for saccharide production), preferably from 0.5 to 20 mass %, more preferably from 3 to 15 mass %, and further preferably from 5 to 10 mass %.

The amount of the mutant BGL of the present invention to be used in the suspension can be suitably determined based on the type, shape, and amount of biomass and the type and properties of enzymes to be used in combination therewith. Preferably, an amount of the mutant BGL to be used in terms of mass based on biomass mass is from 0.04 to 600 mass %, more preferably from 0.1 to 100 mass %, and further preferably from 0.1 to 50 mass %.

Reaction pH of the saccharification treatment is, from a viewpoint of increasing the saccharification efficiency or the saccharide production efficiency and reducing the production cost, preferably from pH 4 to 9, more preferably from pH 5 to 8, and further preferably from pH 5 to 7. Reaction temperature of the saccharification treatment is, from a viewpoint of increasing the saccharification efficiency, increasing the saccharification efficiency or the saccharide production efficiency and reducing the production cost, preferably from 20 to 90° C., more preferably from 25 to 85° C., further preferably from 30 to 80° C., further preferably from 40 to 75° C., further preferably from 45 to 65° C., further preferably from 45 to 60° C., and further preferably from 50 to 60° C. Reaction time of the saccharification treatment can be suitably set in accordance with the type, shape, and amount of biomass and the amount of enzyme(s). Reaction time is, from a viewpoint of increasing the saccharification efficiency or the saccharide production efficiency and reducing the production cost, preferably from 1 to 5 days, more preferably from 1 to 4 days, and further preferably from 1 to 3 days.

Further, the method for producing a saccharide of the present invention further preferably includes, from a viewpoint of increasing the biomass saccharification efficiency or the saccharide production efficiency, a step of pretreating the biomass before saccharifying the biomass using the mutant BGL of the present invention. Examples of the pretreatment include one or more selected from the group consisting of alkali treatment, grinding treatment, and hydrothermal treatment. For the pretreatment, alkali treatment is preferable from a viewpoint of increasing the saccharification efficiency, it is preferable to carry out alkali treatment and grinding treatment from a viewpoint of further increasing the saccharification efficiency, and it is more preferable to carry out alkali treatment and grinding treatment simultaneously. The grinding treatment may be wet grinding or dry grinding, but dry grinding is preferable. More preferably, solid alkali and biomass are together subjected to grinding treatment, to carry out dry grinding in tandem with alkali treatment (alkali-mixed grinding treatment).

Hereinafter, the following substances, production methods, purposes of use, and methods are disclosed in the present Description as exemplary embodiments of the present invention. However, the present invention is not limited to these embodiments.

[1] A mutant β-glucosidase selected from the group consisting of the following (i), (ii), and (iii):

(i) a polypeptide that consists of an amino acid sequence obtained by substituting, with Gln and Thr, an amino acid residue at a position corresponding to position 649 of SEQ ID NO: 1 and an amino acid residue at a position corresponding to position 655 of SEQ ID NO: 1, respectively, in the amino acid sequence as set forth in SEQ ID NO: 1, or an amino acid sequence having at least 90% identity thereto, and has β-glucosidase activity;

(ii) a polypeptide that consists of an amino acid sequence obtained by substituting, with Tyr-Glu-Pro-Ala-Ser-Gly, an amino acid sequence of a region corresponding to the region from position 653 to position 658 of SEQ ID NO:1 in the amino acid sequence as set forth in SEQ ID NO: 1, or an amino acid sequence having at least 90% identity thereto, and has β-glucosidase activity;

(iii) a polypeptide that comprises the polypeptide of (i) or (ii) and has β-glucosidase activity.

[2] The mutant β-glucosidase according to [1], wherein preferably the amino acid sequence as set forth in SEQ ID NO: 1, or an amino acid sequence having at least 90% identity thereto is the amino acid sequence as set forth in SEQ ID NO: 1 or 2, or an amino acid sequence having deletion, substitution or addition of one to several amino acids with respect to the amino acid sequence as set forth in SEQ ID NO: 1 or 2.

[3] The mutant β-glucosidase according to [1] or [2], wherein preferably the mutant β-glucosidase has high protease resistance compared to a parent β-glucosidase.

[4] The mutant β-glucosidase according to [3], wherein the parent β-glucosidase
preferably does not have i) an amino acid residue Gln at a position corresponding to position 649 of SEQ ID NO:1 and an amino acid residue Thr at a position corresponding to position 655 of SEQ ID NO:1; ii) an amino acid sequence Tyr-Glu-Pro-Ala-Ser-Gly in a region corresponding to the region from position 653 to position 658 of SEQ ID NO: 1; or iii) both i) and ii), and
more preferably has i) an amino acid residue Asn at a position corresponding to position 649 and an amino acid residue Gln at a position corresponding to position 655 of SEQ ID NO: 1; ii) an amino acid sequence Asn-Ala-Gln-Val-Ala-Thr in a region corresponding to the region from position 653 to position 658 of SEQ ID NO: 1; or iii) both i) and ii).

[5] A polynucleotide encoding the mutant β-glucosidase of any one of [1] to [4].

[6] A vector comprising the polynucleotide of [5].

[7] A transformant comprising the polynucleotide of [5] or the vector of [6].

[8] The transformant according to [7], wherein the transformant is preferably a filamentous fungus.

[9] A biomass saccharification agent comprising the mutant β-glucosidase of any one of [1] to [5].

[10] A method for producing a saccharide, comprising saccharifying biomass using the mutant β-glucosidase of any one of [1] to [4].

[11] A method for producing a mutant β-glucosidase, comprising:
(a) substituting, with Gln and Thr, an amino acid residue at a position corresponding to position 649 of SEQ ID NO: 1 and an amino acid residue at a position corresponding to position 655 of SEQ ID NO: respectively, in a polypeptide comprising the amino acid sequence as set forth in SEQ ID NO: 1, or an amino acid sequence having at least 90% identity thereto and having β-glucosidase activity or
(b) substituting, with Tyr-Glu-Pro-Ala-Ser-Gly, an amino acid sequence of a region corresponding to the region from position 653 to position 658 of SEQ ID NO:1 in a polypeptide comprising the amino acid sequence as set forth in SEQ ID NO: 1, or an amino acid sequence having at least 90% identity thereto and having β-glucosidase activity.

[12] The method according to [11], wherein the polypeptide comprising the amino acid sequence as set forth in SEQ ID NO: 1, or an amino acid sequence having at least 90% identity thereto and having β-glucosidase activity
preferably does not have i) an amino acid residue Gln at a position corresponding to position 649 of SEQ ID NO:1 and an amino acid residue Thr at a position corresponding to position 655 of SEQ ID NO: 1; ii) an amino acid sequence Tyr-Glu-Pro-Ala-Ser-Gly in a region corresponding to the region from position 653 to position 658 of SEQ ID NO: 1; or iii) both i) and ii), and
more preferably has i) an amino acid residue Asn at a position corresponding to position 649 of SEQ ID NO:1 and an amino acid residue Gln at a position corresponding to position 655 of SEQ ID NO:1; ii) an amino acid sequence Asn-Ala-Gln-Val-Ala-Thr in a region corresponding to the region from position 653 to position 658 of SEQ ID NO: 1; or iii) both i) and ii).

[13] The method according to [11] or [12], wherein preferably the mutant β-glucosidase has high protease resistance compared to the polypeptide comprising the amino acid sequence as set forth in SEQ ID NO: 1, or an amino acid sequence having at least 90% identity thereto and having β-glucosidase activity.

[14] The method according to any one of [11] to [13], wherein preferably the polypeptide comprising the amino acid sequence as set forth in SEQ ID NO: 1, or an amino acid sequence having at least 90% identity thereto and having β-glucosidase activity consists of
the amino acid sequence as set forth in SEQ ID NO: 1 or 2, or
an amino acid sequence having deletion, substitution or addition of one or several amino acids with respect to the amino acid sequence as set forth in SEQ ID NO: 1 or 2.

EXAMPLE

Hereinafter, the present invention is described in further detail in reference with examples but technical scopes of the present invention are not limited to these examples.

Example 1

Construction of Mutant BGL Expression Plasmid (1) Construction of N649Q/Q655T Mutant Expression Plasmid An expression plasmid encoding a mutant (N649Q/Q655T) obtained by introducing N649Q and Q655T into the β-glucosidase 1 (AaBGL1; SEQ ID NO: 1) of *Aspergillus aculeatus*, was constructed.

Mutation was introduced into a gene (AaBGL1 gene, SEQ ID NO: 3) encoding AaBGL1 preprotein having a secretion signal sequence by the PCR-megaprimer method. Namely, using the primers BGL1-N649Q/Q655T and BGL1-R shown in Table 1 and using *Aspergillus aculeatus* No. F-50 strain genome DNA as a template, the gene downstream from the site at which mutation had been introduced in the AaBGL1 gene were amplified using PrimeSTAR HS DNA Polymerase in accordance with the attached protocol. The amplified fragments were isolated and collected by agarose gel electrophoresis. Using the obtained amplified fragments with BGL1-F primer as a megaprimer, PCR was carried out by the same method using the F-50 strain genome DNA as a template to amplify the full-length AaBGL1 gene into which the mutation was introduced. The obtained DNA fragment was cleaved at the primer-derived Not I and Sph I sites and incorporated to the same sites of a filamentous fungus expression vector pNAN8142 (Biosci Biotechnol Biochem, 1996, 60:383-389) to construct the expression plasmid. Correct introduction of the mutation into the DNA fragment was confirmed by sequencing.

(2) Construction of 653YEPASG658 Mutant Expression Plasmid

An expression plasmid encoding a mutant (653YEPASG658) obtained by substituting the amino acid sequence NAQVAT at position 653 to position 658 in the amino acid sequence of AaBGL1 (SEQ ID NO: 1) with an orthologous sequence YEPASG, was constructed. The expression plasmid was constructed by the same procedure as in the above (1) except that the primer BGL1-653YEPASG shown in Table 1 was used in place of the primer BGL1-N649Q/Q655T.

TABLE 1

| Name | Sequence (5' → 3') | SEQ ID: No |
|---|---|---|
| BGL1-F | AACTGCAGGCGGCCGCATCATGAAGCTCAGTTGGCTTG | 4 |
| BGL1-R | AAGCATGCTCATTGCACCTTCGGGAGC | 5 |

| (Mutation primer) Name | Variant | Sequence (5' → 3') | SEQ ID: No |
|---|---|---|---|
| BGL1-N649Q/Q655T | N649Q/Q655T | CAGGTTCTCCAAGCTTCCAGTAACGCTACAGTAGCTACTGA | 6 |
| BGL1-653YEPASG | 653YEPASG658 | CTTCCTCCTATGAACCTGCTAGCGGTGAGACTGGC | 7 |

Example 2

Preparation of Mutant BGL Expression Strain

A transformant was prepared in accordance with the method of Gomi et al. (Agric Biol Chem, 1987, 51:2549-2555). Namely, 5 mL of a Tween/saline solution (0.1% (w/v) Tween (registered trademark) 80, 0.01% NaCl) was added to an *Aspergillus oryzae* (*A. oryzae*) nia D300 strain grown in MM (NH$_4^+$) plate medium (1.0% Glucose, 0.3% Ammonium tartrate, 0.13% KCl, 0.13% MgSO$_4$.7H$_2$O, 0.38%.KH$_2$PO$_4$, 0.00011% Mo$_7$O$_{24}$.4H$_2$O, 0.00011% H$_3$BO$_3$O, 0.00016% CoCl$_2$.6H$_2$O, 0.00016% CuSO$_4$.5H$_2$O, 0.005% EDTA, 0.0005% FeSO$_4$.7H$_2$O, 0.0005% MnCl$_2$.4H$_2$O, 0.0022% ZnSO$_4$.7H$_2$O, pH 6.5) and spores were suspended using a spreader. The spore suspension was added to 200 mL of MM (NH$_4^+$) liquid medium (500-mL Erlenmeyer flask with baffles) and cultured with shaking at 30° C. and 160 rpm overnight. The culturing was finished when suitable growth was achieved and cells were collected on Miracloth and washed with Protoplasting buffer (hereinafter, PB; 0.8M NaCl, 10 mM NaH$_2$PO$_4$). The collected cells were put in a 50-mL centrifuge tube, suspended in 10 mL of PB containing 30 mg of Yatalase (manufactured by TAKARA Bio Inc.) and 50 mg of Lysing enzyme (manufactured by Sigma-Ardrich), and incubated (30° C., 90 min) while gently shaking. Further, the cells were loosened by pipetting every 30 minutes. Thereafter, the suspension was filtered using Miracloth to collect only protoplasts and the obtained filtrate was centrifuged (4° C., 2000 rpm, 5 min). The precipitate was suspended in 10 mL of Transformation buffer I (hereinafter, TB I; 0.8M NaCl, 10 mM Tris-HCl [pH 7.5], 50 mM CaCl$_2$) and centrifuged (4° C., 2000 rpm, 5 min). Thereafter, the supernatant was removed and the precipitate was suspended in 200 µL of TB I to prepare a protoplast solution. The number of protoplasts was confirmed using a microscope and about 10$^7$ cells/mL of protoplasts were used for the subsequent operation.

An equivalent amount of 2×TB I was added to a solution containing about 10 µg of the expression plasmid DNA obtained in Example 1(1) or (2) and the obtained solution was added to the protoplast solution. Further, 0.2 times the amount of Transformation buffer II (hereinafter, TB II; 50% PEG6000, 50 mM Tris-HCl [pH 7.5], 50 mM CaCl$_2$) was added thereto, mixed gently, and allowed to stand for 10 min on ice. Thereafter, 1 mL of TB II was added and allowed to stand at room temperature for 15 min, Subsequently, 10 mL of TB I was added and the solution was centrifuged (4° C., 2000 rpm, 5 min). The supernatant was removed and the precipitate was suspended in 200 µL of TB I, put on Regeneration medium (hereinafter, RE; 1.0% Glucose, 0.3% NaNO$_3$, 4.68% NaCl, 0.13% KCl, 0.13% MgSO$_4$.7H$_2$O, 0.38% KH$_2$PO$_4$, 0.00011% Mo$_7$O$_{24}$.4H$_2$O, 0.00011% H$_3$BO$_3$, 0.00016% CoCl$_2$.6H$_2$O, 0.00016% CuSO$_4$.5H$_2$O, 0.005% EDTA, 0.0005% FeSO$_4$.7H$_2$O, 0.0005% MnCl$_2$.4H$_2$O, 0.0022% ZnSO$_4$.7H$_2$O, pH 6.5), and a top agar (RE, 0.7% agar) was layered on. The obtained transformant was monoclonalized to purify the nucleus. Namely, two microtubes to each of which 200 µL of a Tween/saline solution was added were prepared, and spores of the transformant scraped with the tip of a platinum loop from the RE medium plate in which the transformant had grown was suspended in one of the Tween/saline solutions. 2 µL was taken therefrom and mixed with the other Tween/saline solution to dilute 100-fold. 100 µL of the solution was spread on MM (NO$_3^-$, 0.1% Triton X-100) (NaNO$_3$ was added in place of ammonium tartrate of MM(NH$_4^+$) and further Triton X-100 was added) plate medium and statically cultured at 30° C. for 3 to 4 days. One strain was selected from the colonies grown therein and isolated in MM(NO$_3^+$) plate medium.

Example 3

Protease Resistance of Mutant BGL

The transformant obtained in Example 2 and a wild-type AaBGL1 (WT) expression strain were respectively inoculated in 100 mL of MM (NO$_3^-$) liquid medium and cultured with shaking at 30° C. Every day (day 1 to 8 of culture), 1 mL of the culture supernatant was sampled and 20 µL of which was subjected to SDS-PAGE. For the gel, a polyacrylamide gel consisting of the resolving gel 7.5% and the stacking gel 5% (Acrylamide: N,N'-Methylenebisacrylamide=29.2:0.8) was used. Six×Sample buffer (0.375 M Tris-HCl, 60% Glycerol, 6% 2-Mercaptoethanol, 0.003% Bromophenol blue [pH6.8]) was added to the culture supernatant and treated at 100° C. for 10 minutes to use as a sample. Using a vertical slab electrophoresis system (manufactured by ATTO CORPORATION), electrophoresis was carried out in a phoresis buffer liquid (0.1% SDS, 25 mM Iris base, 192 mM Glycine) under a constant current of 20 mA. After electrophoresis, staining was carried out in a CBB solution (0.2% CBB R-250, 50% Ethanol, 10% Acetic acid) and destained using a destaining solution (10% Methanol, 7.5% Acetic acid). For the protein molecular weight marker, Protein Molecular Weight Marker (Broad) (manufactured by TAKARA Bio Inc.) was used.

Analysis results on the expression products in the culture supernatant by SDS-PAGE are shown in FIGS. 1 to 3. In case of wild-type AaBGL1 (WT), a protein of about 130 kDa was produced on day 3 to 4 of culture but was cleaved into proteins of about 100 kDa and about 30 kDa on and after day 5, and the cleavage of the protein proceeded and the protein of about 30 kDa was lost on and after day 7 (FIG. 1). The loss of the protein of about 30 kDa means the reduction of the AaBGL1 activity. Conversely, in a case of the N649Q/Q655T mutant, a protein of about 130 kDa was observed as the main band even on day 8 of culture, showing having resistance against the cleavage by a protease (FIG. 2). Further, in a case of the 653YEPASG658 mutant, no substantial degradation of a protein of about 130 kDa was found during the culturing period observed (FIG. 3). From the above, it was shown that the mutant BGL of the present invention avoided the degradation by an extracellular protease during the culturing period.

The BGL activity in the culture supernatant of day 6, when the degradation of the about 130 kDa band in WT was observed, was measured by the pNP (p-Nitrophenol) method. The culture supernatant was diluted to prepare an enzyme solution. A 1.5 mM pNP-Glc solution (100 mM Na-acetate buffer, pH 5.0) was used as a substrate solution. An equivalent amount of the 1.5 mM substrate solution was mixed with 100 μL of the enzyme solution preincubated at 37° C. for 5 min to start the enzyme reaction. After reaction at 37° C. for 10 min, 2 mL of a 1M Na$_2$CO$_3$ solution was added to stop the reaction. Then, absorbance at 405 nm was measured to calculate a concentration of released pNP using an extinction coefficient of pNP (ε405 nm=0.0185 mL/nmol cm$^{-1}$), whereby an enzyme activity was determined. For a blank, a solution nonreactive to the enzyme in which 2 mL of 1M Na$_2$CO$_3$ and 100 μL of the substrate solution were sequentially added to 100 μL of the enzyme solution was used. The amount of enzyme which releases 1 μmol of pNP for 1 minute was defined as 1 Unit, and an enzyme activity in the culture supernatant was calculated from the following formula.

Enzyme activity(Unit/mL)=$A$405/18.5×2.2 mL/(10 min)×(1/0.1 mL)×dilution rate of culture supernatant As a result, the N649Q/Q655T mutant and the 653YEPASG658 mutant retains high BGL activities in the culture supernatant of day 6 compared to the wild type.

TABLE 2

| Enzyme | Enzyme activity (U/mL) |
| --- | --- |
| WT | 17.6 |
| 653YEPASG658 | 24.3 |
| N649Q/Q655T | 38.0 |

Example 4

Mutant BGL Activity

The mutant BGL enzyme was purified from the mutant BGL expression strain obtained in Example 2, and the BGL activity thereof was measured by the same procedure as in Example 3 using the pNP (p-Nitrophenol) method. The specific activity of the purified enzyme was calculated by the following formula.

Specific activity(Unit/mg)=enzyme activity (Unit/mL)/protein concentration(mg/mL)

The results are shown in Table 3. The mutant BGLs show the specific activities equivalent to or higher than the intact WT BGL.

TABLE 3

| Enzyme | Specific activity (U/mg) |
| --- | --- |
| WT | 128 |
| 653YEPASG658 | 124 |
| N649Q/Q655T | 160 |

In the above, the embodiments of the present invention were described but it should be understood that these are not intended to limit the present invention to the specific embodiments described. Various other alterations and modifications within the scope of the present invention are obvious by those skilled in the art. The literatures and patent applications cited herein are incorporated as reference as if they were completely described in the present Description.

What is claimed is:

1. A mutant β-glucosidase selected from the group consisting of the following (i), (ii), and (iii):

(i) a polypeptide that consists of an amino acid sequence obtained by substituting, with Gln and Thr, an amino acid residue at a position corresponding to position 649 of SEQ ID NO:1 and an amino acid residue at a position corresponding to position 655 of SEQ ID NO:1, respectively, in the amino acid sequence as set forth in SEQ ID NO: 1, or an amino acid sequence having at least 90% identity thereto, and has β-glucosidase activity;

(ii) a polypeptide that consists of an amino acid sequence obtained by substituting, with Tyr-Glu-Pro-Ala-Ser-Gly, an amino acid sequence of a region corresponding to the region from position 653 to 658 of SEQ ID NO:1 in the amino acid sequence as set forth in SEQ ID NO: 1, or an amino acid sequence having at least 90% identity thereto, and has β-glucosidase activity; and (iii) a polypeptide that comprises the polypeptide of (i) or (ii) and has β-glucosidase activity.

2. The mutant β-glucosidase according to claim 1, wherein the mutant β-glucosidase has high protease resistance compared to a β-glucosidase before the substitution.

3. The mutant β-glucosidase according to claim 2, wherein the β-glucosidase before the substitution has
an amino acid residue Asn at a position corresponding to position 649 of SEQ ID NO:1 and an amino acid residue Gln at a position corresponding to position 655 of SEQ ID NO:1, or
an amino acid sequence Asn-Ala-Gln-Val-Ala-Thr in a region corresponding to the region from position 653 to position 658 of SEQ ID NO: 1.

4. A polynucleotide encoding a mutant β-glucosidase selected from the group consisting of the following (i), (ii), and (iii):
(i) a polypeptide that consists of an amino acid sequence obtained by substituting, with Gln and Thr, an amino acid residue at a position corresponding to position 649 of SEQ ID NO:1 and an amino acid residue at a position corresponding to position 655 of SEQ ID NO:1, respectively, in the amino acid sequence as set forth in SEQ ID NO: 1, or an amino acid sequence having at least 90% identity thereto, and has β-glucosidase activity;
(ii) a polypeptide that consists of an amino acid sequence obtained by substituting, with Tyr-Glu-Pro-Ala-Ser-Gly, an amino acid sequence of a region corresponding to the region from position 653 to 658 of SEQ ID NO:1 in the amino acid sequence as set forth in SEQ ID NO: 1, or an amino acid sequence having at least 90% identity thereto, and has β-glucosidase activity; and
(iii) a polypeptide that comprises the polypeptide of (i) or (ii) and has β-glucosidase activity.

5. A vector comprising the polynucleotide of claim 4.

6. A transformant comprising the polynucleotide of claim 4.

7. The transformant according to claim 6, wherein the transformant is a filamentous fungus.

8. A biomass saccharification agent comprising the mutant β-glucosidase of claim 1.

9. A method for producing a saccharide, comprising saccharifying biomass using the mutant β-glucosidase of claim 1.

10. A method for producing a mutant β-glucosidase, comprising:
(a) substituting, with Gln and Thr, an amino acid residue at a position corresponding to position 649 of SEQ ID NO: 1 and an amino acid residue at a position corresponding to position 655 of SEQ ID NO: 1, respectively, in a polypeptide comprising the amino acid sequence as set forth in SEQ ID NO: 1, or an amino acid sequence having at least 90% identity thereto and having β-glucosidase activity; or
(b) substituting, with Tyr-Glu-Pro-Ala-Ser-Gly, an amino acid sequence of a region corresponding to the region from position 653 to position 658 of SEQ ID NO: 1 in a polypeptide comprising the amino acid sequence as set forth in SEQ ID NO: 1, or an amino acid sequence having at least 90% identity thereto and having β-glucosidase activity.

11. The method according to claim 10, wherein the mutant β-glucosidase has high protease resistance compared to the polypeptide comprising the amino acid sequence as set forth in SEQ ID NO: 1, or an amino acid sequence having at least 90% identity thereto and having β-glucosidase activity.

12. The method according to claim 10, wherein the polypeptide comprising the amino acid sequence as set forth in SEQ ID NO: 1, or an amino acid sequence having at least 90% identity thereto and having β-glucosidase activity has
an amino acid residue Asn at a position corresponding to position 649 of SEQ ID NO: 1 and an amino acid residue Gln at a position corresponding to position 655 of SEQ ID NO: 1, or
an amino acid sequence Asn-Ala-Gln-Val-Ala-Thr in a region corresponding to the region from position 653 to position 658 of SEQ ID NO: 1.

13. A transformant comprising the vector of claim 5.

14. The transformant according to claim 13, wherein the transformant is a filamentous fungus.

15. The mutant β-glucosidase of claim 1, wherein the mutant β-glucosidase is (i) a polypeptide that consists of an amino acid sequence obtained by substituting, with Gln and Thr, an amino acid residue at a position corresponding to position 649 of SEQ ID NO:1 and an amino acid residue at a position corresponding to position 655 of SEQ ID NO:1, respectively, in the amino acid sequence as set forth in SEQ ID NO: 1, or an amino acid sequence having at least 90% identity thereto, and has β-glucosidase activity.

16. The mutant β-glucosidase of claim 1, wherein the mutant β-glucosidase is (ii) a polypeptide that consists of an amino acid sequence obtained by substituting, with Tyr-Glu-Pro-Ala-Ser-Gly, an amino acid sequence of a region corresponding to the region from position 653 to 658 of SEQ ID NO:1 in the amino acid sequence as set forth in SEQ ID NO: 1, or an amino acid sequence having at least 90% identity thereto, and has β-glucosidase activity.

17. The mutant β-glucosidase of claim 1, wherein the mutant β-glucosidase is a polypeptide that comprises the polypeptide of (i) or (ii) and has β-glucosidase activity.

18. The method of claim 9, wherein the mutant β-glucosidase is (i) a polypeptide that consists of an amino acid sequence obtained by substituting, with Gln and Thr, an amino acid residue at a position corresponding to position 649 of SEQ ID NO:1 and an amino acid residue at a position corresponding to position 655 of SEQ ID NO:1, respectively, in the amino acid sequence as set forth in SEQ ID NO: 1, or an amino acid sequence having at least 90% identity thereto, and has β-glucosidase activity.

19. The method of claim 9, wherein the mutant β-glucosidase is (ii) a polypeptide that consists of an amino acid sequence obtained by substituting, with Tyr-Glu-Pro-Ala-Ser-Gly, an amino acid sequence of a region corresponding to the region from position 653 to 658 of SEQ ID NO:1 in the amino acid sequence as set forth in SEQ ID NO: 1, or an amino acid sequence having at least 90% identity thereto, and has β-glucosidase activity.

20. The method of claim 9, wherein the mutant β-glucosidase is a polypeptide that comprises the polypeptide of (i) or (ii) and has β-glucosidase activity.

* * * * *

SEQUENCE LISTING

<160> NUMBER OF SEQ ID NOS: 7

<210> SEQ ID NO 1
<211> LENGTH: 841
<212> TYPE: PRT
<213> ORGANISM: Aspergillus aculeatus

<400> SEQUENCE: 1

Asp Glu Leu Ala Phe Ser Pro Pro Phe Tyr Pro Ser Pro Trp Ala Asn
1               5                   10                  15

Gly Gln Gly Glu Trp Ala Glu Ala Tyr Gln Arg Ala Val Ala Ile Val
            20                  25                  30

Ser Gln Met Thr Leu Asp Glu Lys Val Asn Leu Thr Thr Gly Thr Gly
        35                  40                  45

Trp Glu Leu Glu Lys Cys Val Gly Gln Thr Gly Gly Val Pro Arg Leu
    50                  55                  60

Asn Ile Gly Gly Met Cys Leu Gln Asp Ser Pro Leu Gly Ile Arg Asp
65                  70                  75                  80

Ser Asp Tyr Asn Ser Ala Phe Pro Ala Gly Val Asn Val Ala Ala Thr
                85                  90                  95

```
Trp Asp Lys Asn Leu Ala Tyr Leu Arg Gly Gln Ala Met Gly Gln Glu
            100                 105                 110

Phe Ser Asp Lys Gly Ile Asp Val Gln Leu Gly Pro Ala Ala Gly Pro
            115                 120                 125

Leu Gly Arg Ser Pro Asp Gly Arg Asn Trp Glu Gly Phe Ser Pro
        130                 135                 140

Asp Pro Ala Leu Thr Gly Val Leu Phe Ala Glu Thr Ile Lys Gly Ile
145                 150                 155                 160

Gln Asp Ala Gly Val Val Ala Thr Ala Lys His Tyr Ile Leu Asn Glu
                165                 170                 175

Gln Glu His Phe Arg Gln Val Ala Glu Ala Ala Gly Tyr Gly Phe Asn
            180                 185                 190

Ile Ser Asp Thr Ile Ser Ser Asn Val Asp Asp Lys Thr Ile His Glu
        195                 200                 205

Met Tyr Leu Trp Pro Phe Ala Asp Ala Val Arg Ala Gly Val Gly Ala
        210                 215                 220

Ile Met Cys Ser Tyr Asn Gln Ile Asn Asn Ser Tyr Gly Cys Gln Asn
225                 230                 235                 240

Ser Tyr Thr Leu Asn Lys Leu Leu Lys Ala Glu Leu Gly Phe Gln Gly
                245                 250                 255

Phe Val Met Ser Asp Trp Gly Ala His His Ser Gly Val Gly Ser Ala
            260                 265                 270

Leu Ala Gly Leu Asp Met Ser Met Pro Gly Asp Ile Thr Phe Asp Ser
        275                 280                 285

Ala Thr Ser Phe Trp Gly Thr Asn Leu Thr Ile Ala Val Leu Asn Gly
        290                 295                 300

Thr Val Pro Gln Trp Arg Val Asp Asp Met Ala Val Arg Ile Met Ala
305                 310                 315                 320

Ala Tyr Tyr Lys Val Gly Arg Asp Arg Leu Tyr Gln Pro Pro Asn Phe
                325                 330                 335

Ser Ser Trp Thr Arg Asp Glu Tyr Gly Phe Lys Tyr Phe Tyr Pro Gln
            340                 345                 350

Glu Gly Pro Tyr Glu Lys Val Asn His Phe Val Asn Val Gln Arg Asn
        355                 360                 365

His Ser Glu Val Ile Arg Lys Leu Gly Ala Asp Ser Thr Val Leu Leu
        370                 375                 380

Lys Asn Asn Asn Ala Leu Pro Leu Thr Gly Lys Glu Arg Lys Val Ala
385                 390                 395                 400

Ile Leu Gly Glu Asp Ala Gly Ser Asn Ser Tyr Gly Ala Asn Gly Cys
                405                 410                 415

Ser Asp Arg Gly Cys Asp Asn Gly Thr Leu Ala Met Ala Trp Gly Ser
            420                 425                 430

Gly Thr Ala Glu Phe Pro Tyr Leu Val Thr Pro Glu Gln Ala Ile Gln
        435                 440                 445

Ala Glu Val Leu Lys His Lys Gly Ser Val Tyr Ala Ile Thr Asp Asn
        450                 455                 460

Trp Ala Leu Ser Gln Val Glu Thr Leu Ala Lys Gln Ala Ser Val Ser
465                 470                 475                 480

Leu Val Phe Val Asn Ser Asp Ala Gly Glu Gly Tyr Ile Ser Val Asp
                485                 490                 495

Gly Asn Glu Gly Asp Arg Asn Asn Leu Thr Leu Trp Lys Asn Gly Asp
            500                 505                 510
```

Asn Leu Ile Lys Ala Ala Ala Asn Cys Asn Asn Thr Ile Val Val
            515                 520                 525

Ile His Ser Val Gly Pro Val Leu Val Asp Glu Trp Tyr Asp His Pro
        530                 535                 540

Asn Val Thr Ala Ile Leu Trp Ala Gly Leu Pro Gly Gln Glu Ser Gly
545                 550                 555                 560

Asn Ser Leu Ala Asp Val Leu Tyr Gly Arg Val Asn Pro Gly Ala Lys
                565                 570                 575

Ser Pro Phe Thr Trp Gly Lys Thr Arg Glu Ala Tyr Gly Asp Tyr Leu
            580                 585                 590

Val Arg Glu Leu Asn Asn Gly Asn Gly Ala Pro Gln Asp Asp Phe Ser
        595                 600                 605

Glu Gly Val Phe Ile Asp Tyr Arg Gly Phe Asp Lys Arg Asn Glu Thr
    610                 615                 620

Pro Ile Tyr Glu Phe Gly His Gly Leu Ser Tyr Thr Thr Phe Asn Tyr
625                 630                 635                 640

Ser Gly Leu His Ile Gln Val Leu Asn Ala Ser Ser Asn Ala Gln Val
                645                 650                 655

Ala Thr Glu Thr Gly Ala Ala Pro Thr Phe Gly Gln Val Gly Asn Ala
            660                 665                 670

Ser Asp Tyr Val Tyr Pro Glu Gly Leu Thr Arg Ile Ser Lys Phe Ile
        675                 680                 685

Tyr Pro Trp Leu Asn Ser Thr Asp Leu Lys Ala Ser Ser Gly Asp Pro
    690                 695                 700

Tyr Tyr Gly Val Asp Thr Ala Glu His Val Pro Glu Gly Ala Thr Asp
705                 710                 715                 720

Gly Ser Pro Gln Pro Val Leu Pro Ala Gly Gly Ser Gly Gly Asn
                725                 730                 735

Pro Arg Leu Tyr Asp Glu Leu Ile Arg Val Ser Val Thr Val Lys Asn
            740                 745                 750

Thr Gly Arg Val Ala Gly Asp Ala Val Pro Gln Leu Tyr Val Ser Leu
        755                 760                 765

Gly Gly Pro Asn Glu Pro Lys Val Val Leu Arg Lys Phe Asp Arg Leu
    770                 775                 780

Thr Leu Lys Pro Ser Glu Glu Thr Val Trp Thr Thr Thr Leu Thr Arg
785                 790                 795                 800

Arg Asp Leu Ser Asn Trp Asp Val Ala Ala Gln Asp Trp Val Ile Thr
                805                 810                 815

Ser Tyr Pro Lys Lys Val His Val Gly Ser Ser Ser Arg Gln Leu Pro
            820                 825                 830

Leu His Ala Ala Leu Pro Lys Val Gln
        835                 840

<210> SEQ ID NO 2
<211> LENGTH: 860
<212> TYPE: PRT
<213> ORGANISM: Aspergillus aculeatus

<400> SEQUENCE: 2

Met Lys Leu Ser Trp Leu Glu Ala Ala Leu Thr Ala Ala Ser Val
1               5                   10                  15

Val Ser Ala Asp Glu Leu Ala Phe Ser Pro Pro Phe Tyr Pro Ser Pro
            20                  25                  30

Trp Ala Asn Gly Gln Gly Glu Trp Ala Glu Ala Tyr Gln Arg Ala Val
        35                  40                  45

-continued

```
Ala Ile Val Ser Gln Met Thr Leu Asp Glu Lys Val Asn Leu Thr Thr
         50                  55                  60
Gly Thr Gly Trp Glu Leu Glu Lys Cys Val Gly Gln Thr Gly Gly Val
 65                  70                  75                  80
Pro Arg Leu Asn Ile Gly Gly Met Cys Leu Gln Asp Ser Pro Leu Gly
                 85                  90                  95
Ile Arg Asp Ser Asp Tyr Asn Ser Ala Phe Pro Ala Gly Val Asn Val
            100                 105                 110
Ala Ala Thr Trp Asp Lys Asn Leu Ala Tyr Leu Arg Gly Gln Ala Met
        115                 120                 125
Gly Gln Glu Phe Ser Asp Lys Gly Ile Asp Val Gln Leu Gly Pro Ala
130                 135                 140
Ala Gly Pro Leu Gly Arg Ser Pro Asp Gly Gly Arg Asn Trp Glu Gly
145                 150                 155                 160
Phe Ser Pro Asp Pro Ala Leu Thr Gly Val Leu Phe Ala Glu Thr Ile
                165                 170                 175
Lys Gly Ile Gln Asp Ala Gly Val Val Ala Thr Ala Lys His Tyr Ile
            180                 185                 190
Leu Asn Glu Gln Glu His Phe Arg Gln Val Ala Glu Ala Ala Gly Tyr
        195                 200                 205
Gly Phe Asn Ile Ser Asp Thr Ile Ser Ser Asn Val Asp Asp Lys Thr
210                 215                 220
Ile His Glu Met Tyr Leu Trp Pro Phe Ala Asp Ala Val Arg Ala Gly
225                 230                 235                 240
Val Gly Ala Ile Met Cys Ser Tyr Asn Gln Ile Asn Asn Ser Tyr Gly
                245                 250                 255
Cys Gln Asn Ser Tyr Thr Leu Asn Lys Leu Leu Lys Ala Glu Leu Gly
            260                 265                 270
Phe Gln Gly Phe Val Met Ser Asp Trp Gly Ala His His Ser Gly Val
        275                 280                 285
Gly Ser Ala Leu Ala Gly Leu Asp Met Ser Met Pro Gly Asp Ile Thr
290                 295                 300
Phe Asp Ser Ala Thr Ser Phe Trp Gly Thr Asn Leu Thr Ile Ala Val
305                 310                 315                 320
Leu Asn Gly Thr Val Pro Gln Trp Arg Val Asp Asp Met Ala Val Arg
                325                 330                 335
Ile Met Ala Ala Tyr Tyr Lys Val Gly Arg Asp Arg Leu Tyr Gln Pro
            340                 345                 350
Pro Asn Phe Ser Ser Trp Thr Arg Asp Glu Tyr Gly Phe Lys Tyr Phe
        355                 360                 365
Tyr Pro Gln Glu Gly Pro Tyr Glu Lys Val Asn His Phe Val Asn Val
370                 375                 380
Gln Arg Asn His Ser Glu Val Ile Arg Lys Leu Gly Ala Asp Ser Thr
385                 390                 395                 400
Val Leu Leu Lys Asn Asn Asn Ala Leu Pro Leu Thr Gly Lys Glu Arg
                405                 410                 415
Lys Val Ala Ile Leu Gly Glu Asp Ala Gly Ser Asn Ser Tyr Gly Ala
            420                 425                 430
Asn Gly Cys Ser Asp Arg Gly Cys Asp Asn Gly Thr Leu Ala Met Ala
        435                 440                 445
Trp Gly Ser Gly Thr Ala Glu Phe Pro Tyr Leu Val Thr Pro Glu Gln
450                 455                 460
```

```
Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
            485                 490                 495

Ser Val Ser Leu Val Phe Val Asn Ser Asp Ala Gly Glu Gly Tyr Ile
        500                 505                 510

Ser Val Asp Gly Asn Glu Gly Asp Arg Asn Asn Leu Thr Leu Trp Lys
        515                 520                 525

Asn Gly Asp Asn Leu Ile Lys Ala Ala Asn Cys Asn Asn Thr
    530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
            565                 570                 575

Glu Ser Gly Asn Ser Leu Ala Asp Val Leu Tyr Gly Arg Val Asn Pro
        580                 585                 590

Gly Ala Lys Ser Pro Phe Thr Trp Gly Lys Thr Arg Glu Ala Tyr Gly
        595                 600                 605

Asp Tyr Leu Val Arg Glu Leu Asn Asn Gly Asn Gly Ala Pro Gln Asp
        610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
            645                 650                 655

Phe Asn Tyr Ser Gly Leu His Ile Gln Val Leu Asn Ala Ser Ser Asn
        660                 665                 670

Ala Gln Val Ala Thr Glu Thr Gly Ala Ala Pro Thr Phe Gly Gln Val
        675                 680                 685

Gly Asn Ala Ser Asp Tyr Val Tyr Pro Glu Gly Leu Thr Arg Ile Ser
    690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
            725                 730                 735

Ala Thr Asp Gly Ser Pro Gln Pro Val Leu Pro Ala Gly Gly Gly Ser
        740                 745                 750

Gly Gly Asn Pro Arg Leu Tyr Asp Glu Leu Ile Arg Val Ser Val Thr
    755                 760                 765

Val Lys Asn Thr Gly Arg Val Ala Gly Asp Ala Val Pro Gln Leu Tyr
770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
            805                 810                 815

Leu Thr Arg Arg Asp Leu Ser Asn Trp Asp Val Ala Ala Gln Asp Trp
        820                 825                 830

Val Ile Thr Ser Tyr Pro Lys Lys Val His Val Gly Ser Ser Ser Arg
        835                 840                 845

Gln Leu Pro Leu His Ala Ala Leu Pro Lys Val Gln
    850                 855                 860

<210> SEQ ID NO 3
<211> LENGTH: 2812
<212> TYPE: DNA
```

<213> ORGANISM: Aspergillus aculeatus

<400> SEQUENCE: 3

| | | | | | |
|---|---|---|---|---|---|
| ccatggtacc | cggatcctcg | cttcaacatc | tttctcaaat | tctcgagagc | gcaagctgtg | 60 |
| tggctggcta | gctcgttgct | tcctctttct | tcagctacct | ctacgccatc | atgaagctca | 120 |
| gttggcttga | ggcggctgcc | ttgacggctg | cttcagtcgt | cagcgctgat | gaactggcgt | 180 |
| tctctcctcc | tttctacccc | tctccgtggg | ccaatggcca | gggagagtgg | gcggaagcct | 240 |
| accagcgtgc | agtggccatt | gtatcccaga | tgactctgga | tgagaaggtc | aacctgacca | 300 |
| ccggaactgg | atgggagctg | agaagtgcg | tcggtcagac | tggtggtgtc | caagactga | 360 |
| acatcggtgg | catgtgtctt | caggacagtc | ccttgggaat | tcgtgatagt | gactacaatt | 420 |
| cggctttccc | tgctggtgtc | aacgttgctg | cgacatggga | caagaacctt | gcttatctac | 480 |
| gtggtcaggc | tatgggtcaa | gagttcagtg | acaaaggaat | tgatgttcaa | ttgggaccgg | 540 |
| ccgcgggtcc | cctcggcagg | agccctgatg | gaggtcgcaa | ctgggaaggt | ttctctccag | 600 |
| acccggctct | tactggtgtg | ctcttttgcgg | agacgattaa | gggtattcaa | gacgctggtg | 660 |
| tcgtggcgac | agccaagcat | tacattctca | atgagcaaga | gcatttccgc | caggtcgcag | 720 |
| aggctgcggg | ctacgggattc | aatatctccg | acacgatcag | ctctaacgtt | gatgacaaga | 780 |
| ccattcatga | aatgtacctc | tggcccttcg | cggatgccgt | tcgcgccggc | gttggcgcca | 840 |
| tcatgtgttc | ctacaaccag | atcaacaaca | gctacggttg | ccagaacagt | tacactctga | 900 |
| acaagcttct | gaaggccgag | ctcggcttcc | agggctttgt | gatgtctgac | tggggtgctc | 960 |
| accacagtgg | tgttggctct | gctttggccg | gcttggatat | gtcaatgcct | ggcgatatca | 1020 |
| ccttcgattc | tgccactagt | ttctggggta | ccaacctgac | cattgctgtg | ctcaacggta | 1080 |
| ccgtcccgca | gtgcgcgtt | gacgacatgg | ctgtccgtat | catggctgcc | tactacaagg | 1140 |
| ttggccgcga | ccgcctgtac | cagccgccta | acttcagctc | ctggactcgc | gatgaatacg | 1200 |
| gcttcaagta | tttctacccc | caggaagggc | cctatgagaa | ggtcaatcac | tttgtcaatg | 1260 |
| tgcagcgcaa | ccacagcgag | gttattcgca | agttgggagc | agacagtact | gttctactga | 1320 |
| agaacaacaa | tgccctgccg | ctgaccggaa | aggagcgcaa | agttgcgatc | ctgggtgaag | 1380 |
| atgctggatc | caactcgtac | ggtgccaatg | gctgctctga | ccgtggctgt | gacaacggta | 1440 |
| ctcttgctat | ggcttggggt | agcggcactg | ccgaattccc | atatctcgtg | accctgagc | 1500 |
| aggctattca | agccgaggtg | ctcaagcata | agggcagcgt | ctacgccatc | acggacaact | 1560 |
| gggcgctgag | ccaggtggag | accctcgcta | acaagccag | tgtctctctt | gtatttgtca | 1620 |
| actcggacgc | gggagagggc | tatatctccg | tggacggaaa | cgagggcgac | cgcaacaacc | 1680 |
| tcaccctctg | gaagaacggc | gacaacctca | tcaaggctgc | tgcaaacaac | tgcaacaaca | 1740 |
| ccatcgttgt | catccactcc | gttggacctg | ttttggttga | cgagtggtat | gaccacccca | 1800 |
| acgttactgc | catcctctgg | gcgggcttgc | ctggccagga | gtctggcaac | tccttggctg | 1860 |
| acgtgctcta | cggccgcgtc | aacccgggcg | ccaaatctcc | attcacctgg | ggcaagacga | 1920 |
| gggaggcgta | cggggattac | cttgtccgtg | agctcaacaa | cggcaacgga | gctccccaag | 1980 |
| atgatttctc | ggaaggtgtt | ttcattgact | accgcggatt | cgacaagcgc | aatgagaccc | 2040 |
| cgatctacga | gttcggacat | ggtctgagct | acaccacttt | caactactct | ggccttcaca | 2100 |
| tccaggttct | caacgcttcc | tccaacgctc | aagtagccac | tgagactggc | gccgctccca | 2160 |
| ccttcggaca | agtcggcaat | gcctctgact | acgtgtaccc | tgagggattg | accagaatca | 2220 |
| gcaagttcat | ctatccctgg | cttaattcca | cagacctgaa | ggcctcatct | ggcgacccgt | 2280 |

```
actatggagt cgacaccgcg gagcacgtgc ccgagggtgc tactgatggc tctccgcagc    2340
ccgttctgcc tgccggtggt ggctctggtg gtaacccgcg cctctacgat gagttgatcc    2400
gtgtttcggt gacagtcaag aacactggtc gtgttgccgg tgatgctgtg cctcaattgt    2460
atgtttccct tggtggaccc aatgagccca aggttgtgtt gcgcaaattc gaccgcctca    2520
ccctcaagcc ctccgaggag acggtgtgga cgactaccct gacccgccgc gatctgtcta    2580
actgggacgt tgcggctcag gactgggtca tcacttctta cccgaagaag gtccatgttg    2640
gtagctcttc gcgtcagctg ccccttcacg cggcgctccc gaaggtgcaa tgagcagctg    2700
aaggtgttgt gaaggaaggg ctttgggcct cagcttcagc ttgcagctga agatgatgta    2760 tacattttc ccaagtcgta gagactacga atttaatgac tatgatgctg tc             2812

<210> SEQ ID NO 4
<211> LENGTH: 38
<212> TYPE: DNA
<213> ORGANISM: Artificial
<220> FEATURE:
<223> OTHER INFORMATION: BGL1-F

<400> SEQUENCE: 4
aactgcaggc ggccgcatca tgaagctcag ttggcttg                              38

<210> SEQ ID NO 5
<211> LENGTH: 27
<212> TYPE: DNA
<213> ORGANISM: Artificial
<220> FEATURE:
<223> OTHER INFORMATION: BGL1-R

<400> SEQUENCE: 5
aagcatgctc attgcacctt cgggagc                                          27

<210> SEQ ID NO 6
<211> LENGTH: 41
<212> TYPE: DNA
<213> ORGANISM: Artificial
<220> FEATURE:
<223> OTHER INFORMATION: BGL1-N649Q/Q655T

<400> SEQUENCE: 6
caggttctcc aagcttccag taacgctaca gtagctactg a                          41

<210> SEQ ID NO 7
<211> LENGTH: 35
<212> TYPE: DNA
<213> ORGANISM: Artificial
<220> FEATURE:
<223> OTHER INFORMATION: BGL1-653YEPASG658

<400> SEQUENCE: 7
cttcctccta tgaacctgct agcggtgaga ctggc                                 35
```